(12) United States Patent
Cheng et al.

(10) Patent No.: US 9,693,838 B2
(45) Date of Patent: Jul. 4, 2017

(54) DUAL-BARREL CARTRIDGE ADAPTOR

(71) Applicant: Phillip Phung-I Ho, Santa Barbara, CA (US)

(72) Inventors: Chieh-Yu Cheng, New Taipei (TW); Chu-Chen Wang, New Taipei (TW); Chung-Chieh Lee, New Taipei (TW)

(73) Assignee: Phillip Phung-I Ho, Santa Barbara, CA (US)

( * ) Notice: Subject to any disclaimer, the term of this patent is extended or adjusted under 35 U.S.C. 154(b) by 21 days.

(21) Appl. No.: 14/822,199

(22) Filed: Aug. 10, 2015

(65) Prior Publication Data
US 2017/0042646 A1    Feb. 16, 2017

(51) Int. Cl.
*B67D 7/70* (2010.01)
*A61C 9/00* (2006.01)

(52) U.S. Cl.
CPC .................. *A61C 9/0026* (2013.01)

(58) Field of Classification Search
CPC ..................................................... B61C 9/0026
USPC ..... 222/137, 132–136, 145.1–145.8; 604/82; 141/18, 214, 237
See application file for complete search history.

(56) References Cited

U.S. PATENT DOCUMENTS

| | | | | |
|---|---|---|---|---|
| 5,651,397 A | * | 7/1997 | Black ................... | A61C 5/064 141/18 |
| 7,575,131 B2 | * | 8/2009 | Feinberg .......... | A61B 17/00491 222/1 |
| 8,746,509 B2 | * | 6/2014 | An ....................... | A61C 9/0026 222/145.6 |
| 8,875,947 B2 | * | 11/2014 | Obrist ................. | B65D 81/325 222/137 |
| 9,289,797 B2 | * | 3/2016 | Pappalardo ....... | B05C 17/00506 |
| 2014/0110435 A1 | * | 4/2014 | Pappalardo .......... | B01F 5/0082 222/145.5 |

* cited by examiner

*Primary Examiner* — Lien Ngo
(74) *Attorney, Agent, or Firm* — C. G. Mersereau; Nikolai & Mersereau, P.A.

(57) ABSTRACT

The invention is related to a cartridge adaptor which comprises a first dual-barrel cartridge, a housing, an adaptor and a second dual-barrel cartridge. The first dual-barrel cartridge comprises two openings and is disposed in the housing. The housing comprises a first fastening component. The adaptor has two inlets which opposite to the two inlets. The two inlets are respectively mounted into and communicate with the two openings of the first dual-barrel cartridge. The two outlets communicate with the two inlets. The second dual-barrel cartridge comprises two openings and a second fastening component which is complementary to the first fastening component of the housing. The two openings of the second dual-barrel cartridge communicates with the two outlets of the adaptor. The invention prevents the remaining unmixed component substances from oozing out of the two inlets or the two outlets of the adaptor during the transfer process of the remaining component substances.

12 Claims, 5 Drawing Sheets

DUAL-BARREL CARTRIDGE ADAPTOR

BACKGROUND OF THE INVENTION

1. Field of the Invention

The present invention relates to an adaptor, especially to an adaptor with a fastening component for connecting two dual-barrel cartridges.

2. Description of the Prior Art

As a user uses the conventional cartridge apparatus a few times for mixing and delivering multi-component substances, particularly for expressing said mixed substances onto a tray during the taking of a dental impression, the remaining unmixed substances inside the barrels get to a point where there are not enough substances for another impression and the substances must be discarded. It results in an undesirable waste of the multi-component substances.

SUMMARY OF THE INVENTION

To overcome the shortcomings, the present invention provides a cartridge adaptor to mitigate or obviate the aforementioned problems.

The main objective of the invention is to provide a cartridge adaptor. The cartridge adaptor in accordance with the present invention has a first dual-barrel cartridge, a housing and an adaptor.

The first dual-barrel cartridge comprises two openings and the first dual-barrel cartridge is disposed in the housing. The housing comprises a front retaining base, a fixed portion and a first fastening component. The front retaining base is positioned at one end of the housing and the front retaining base has two recesses positioned opposite each other. The fixed portion comprises two lateral sides and a first fastening component. Each of the two lateral sides of the fixed portion is respectively mounted in one of the two recesses of the front retaining base. The first fastening component is positioned between the two lateral sides of the fixed portion.

The adaptor has a first plate, two inlets and two outlets. The first plate comprises a front surface and a rear surface opposite to the front surface. Each of the two inlets is separately connected to the front surface of the first plate and each of the two inlets is respectively mounted into and communicates with each of the two openings of the first dual-barrel cartridge. Each of the two outlets is separately connected to the rear surface of the first plate and one of the two outlets communicates with one of the two inlets, and the other of the two outlets communicates with the other of the two inlets.

The cartridge adaptor in accordance with the present invention further comprises a second dual-barrel cartridge. The second dual-barrel cartridge comprises two openings and a second fastening component. Each of the two openings of the second dual-barrel cartridge is respectively connected to and communicates with each of the two outlets of the adaptor. The second fastening component is formed between the two openings of the dual-barrel cartridge and is complementary to the first fastening component of the housing.

The cartridge adaptor in accordance with the present invention further comprises a lid. The lid has a second plate, two covers and a third fastening component. The second plate comprises a surface, two lateral sides and a third fastening component. The two lateral sides are disposed at side edges of the surface of the lid. Each of the two covers is formed on the surface of the second plate and is complementary to the second fastening component of the second dual-barrel cartridge.

Preferably, the lid further comprises a groove formed on one of the two lateral sides.

Preferably, the lid further comprises a protrusion, wherein the protrusion is disposed on the groove of the second plate.

Preferably, each of the two outlets of the adaptor further comprises a back outlet and a front outlet. One end of each of the back outlets of the two outlets is connected to the rear surface of the first plate, and the outside diameter of each of the back outlets is equal to the outside diameter of each of the two openings of the second dual-barrel cartridge. Each of the front outlets of the two outlets is respectively connected to and communicates with each of the back outlets of the two outlets opposite to the rear surface of the first plate, and the outside diameter of each of the front outlets is smaller than the outside diameter of each of the back outlets but is equal to the inside diameter of each of the two openings of the second dual-barrel cartridge.

Preferably, the outside diameter of the back outlet is equal to the outside diameter of each of the two openings of the second dual-barrel cartridge. The outside diameter of the front outlet is bigger than the outside diameter of the back outlet, and the inner diameter of the front outlet is equal to the outside diameter of each of the two openings of the second dual-barrel cartridge.

Preferably, the first fastening component of the housing is a first hook.

Preferably, the second fastening component of the second dual-barrel cartridges is a second hook.

Preferably, the third fastening component of the lid is a third hook.

Preferably, each of the two covers further comprises an inner wall, an inner protrusion and a recess. Each of the inner protrusions is disposed within each of the two covers and mounted into each of the two openings of the second dual-barrel cartridge. Each of the recesses is positioned between the inner wall and the inner protrusion of each of the two covers and each of the recesses is respectively mounted by each of the two openings of the second dual-barrel cartridge.

Preferably, the diameter of each of the inner protrusions of the two covers is equal to the inside diameter of each of the two openings of the second dual-barrel cartridge.

Preferably, the diameter of the inner wall of each of the two covers is equal to the outside diameter of each of the two openings of the second dual-barrel cartridge.

The cartridge adaptor of the present invention helps two different component substances respectively remain in each channel of the first dual-barrel cartridge to be transferred into each channel of the second dual-barrel cartridge, such that the remaining component substances can be stored in the second dual-barrel cartridge for further use. Besides, the first fastening component of the housing complementary to the second fastening component of the second dual-barrel cartridge helps to fasten the first dual-barrel cartridge with the second dual-barrel cartridge tightly and prevents the remaining component substances from oozing out of the two inlets or the two outlets of the adaptor during the process of transferring the remaining component substances.

DETAILED DESCRIPTION OF THE PREFERRED EMBODIMENTS

Figure 1:
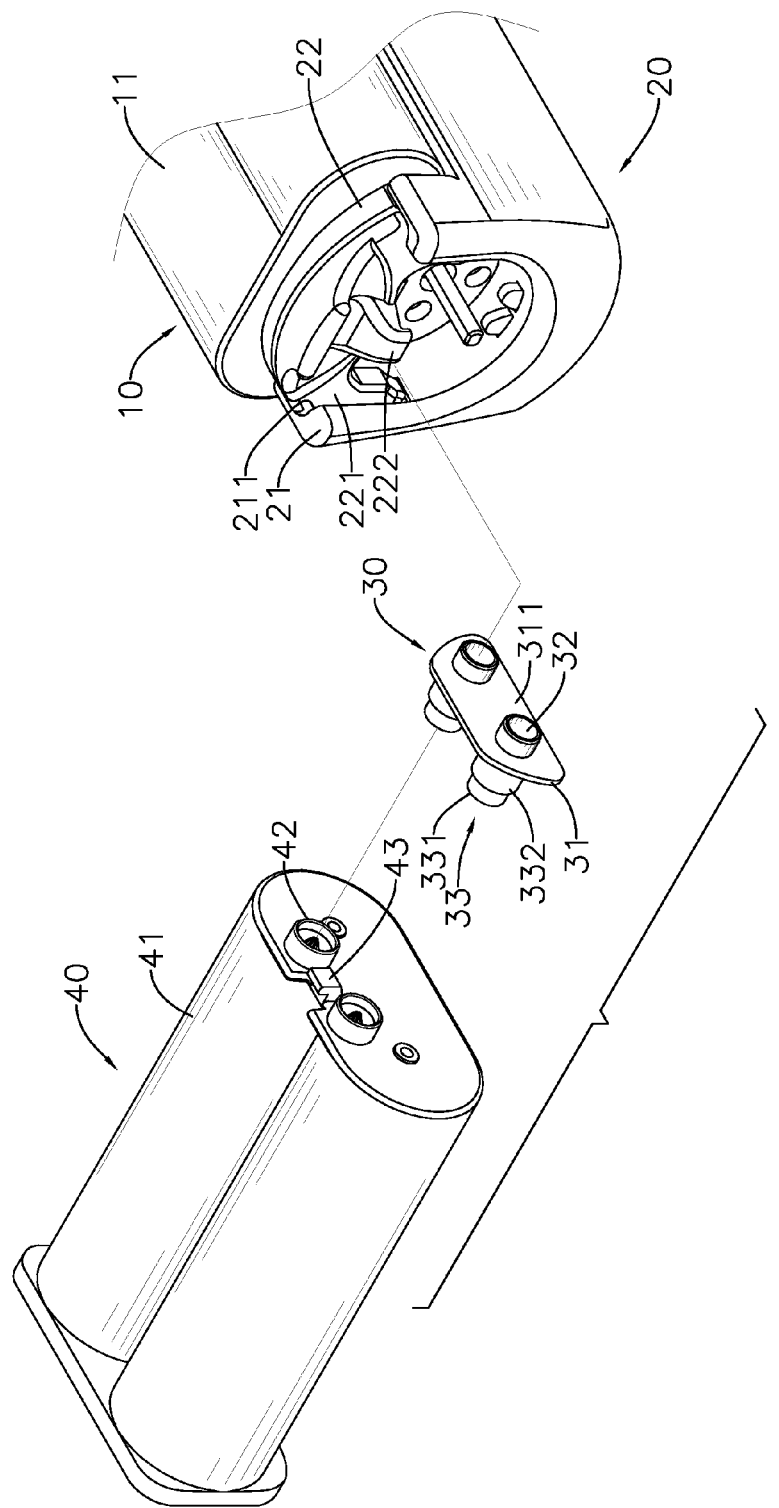
FIG. 1 is a perspective exploded view of a cartridge adaptor in accordance with the present invention.
Figure 2:
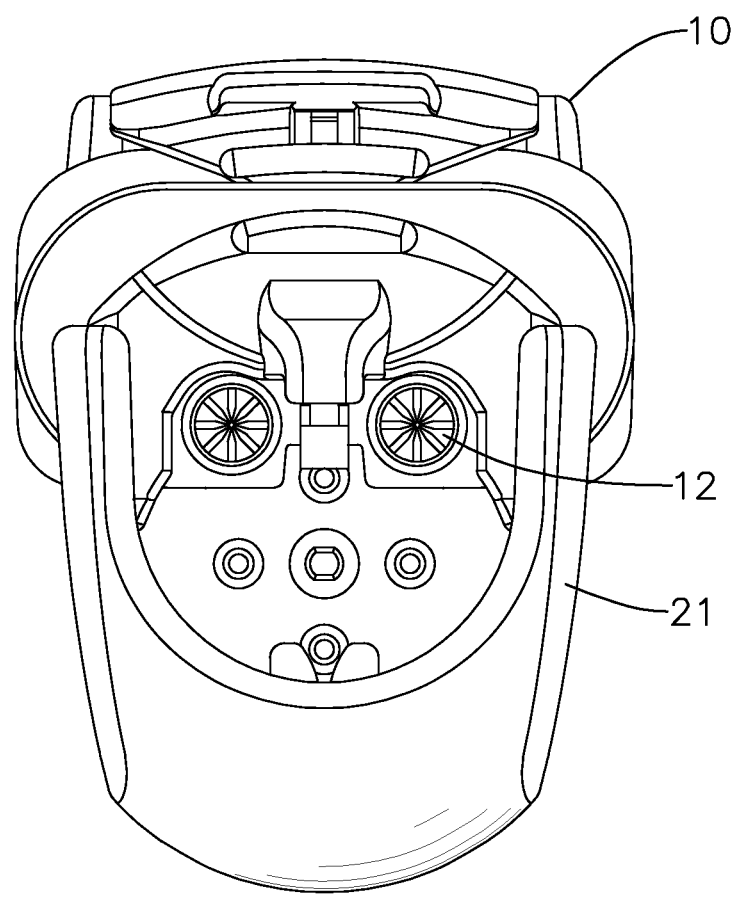
FIG. 2 is a front view of the cartridge adaptor in accordance with the present invention.
Figure 3:
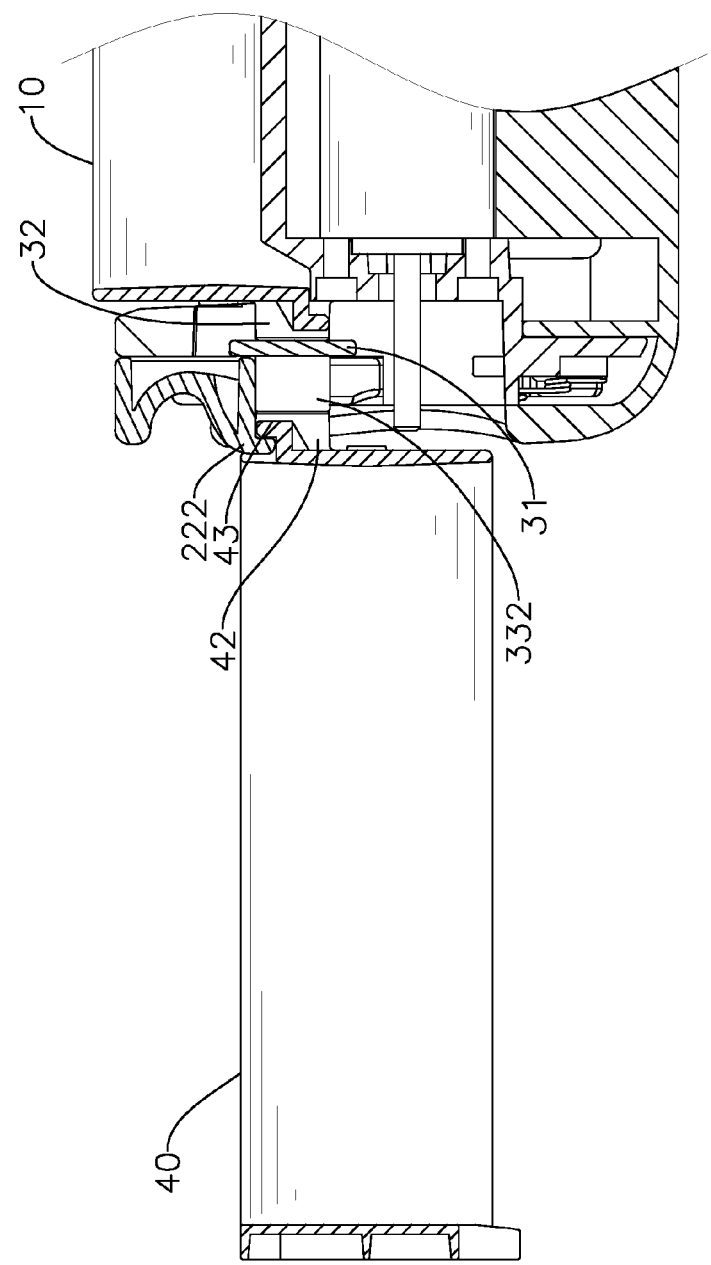
FIG. 3 is a cross-sectional side view of the cartridge adaptor in FIG. 1.
Figure 4:
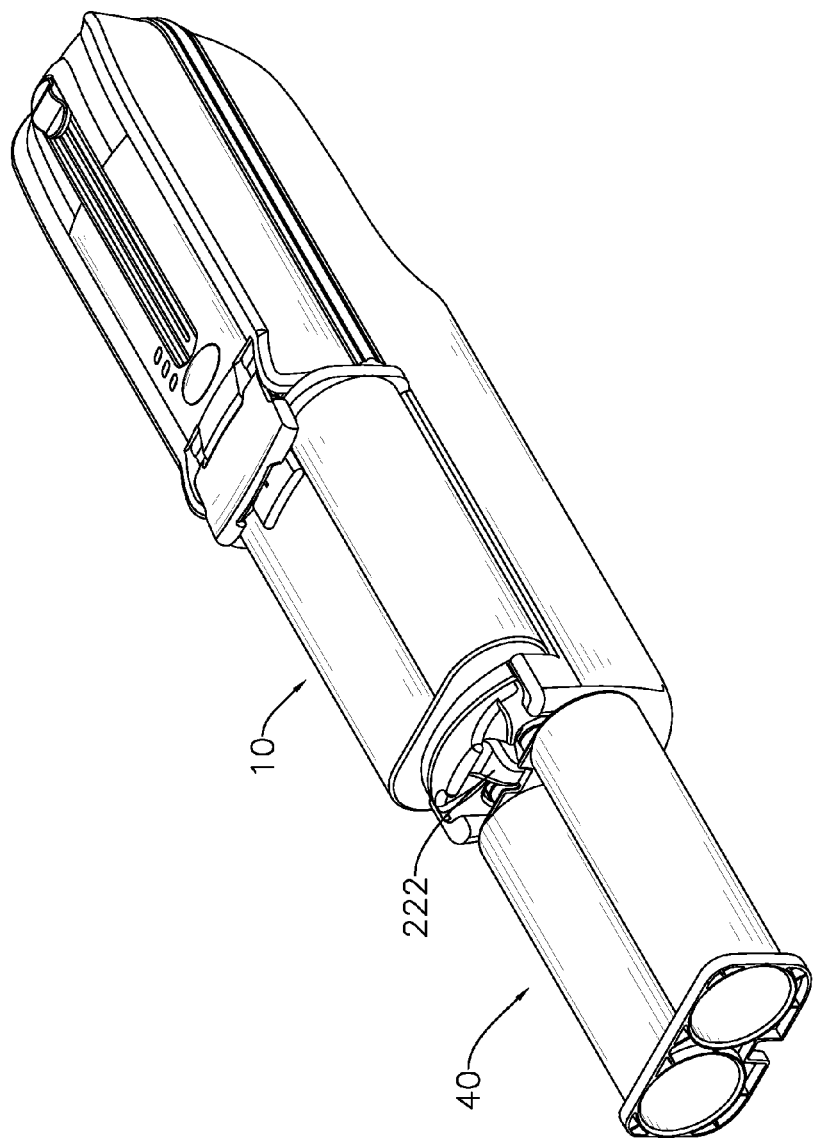
FIG. 4 is a perspective view of the cartridge adaptor in FIG. 1.

With references to FIGS. 1 and 2, a cartridge adaptor in accordance with the present invention comprises a first dual-barrel cartridge 10, a housing 20, an adaptor 30, and a second dual-barrel cartridge 40. The first dual-barrel cartridge 10 is disposed in the housing 20. The adaptor 30 connects the first dual-barrel cartridge 10 and the second dual-barrel cartridge 40.

The first dual-barrel cartridge 10 comprises two chambers 11 and two openings 12. Each of the two openings 12 is circular and respectively communicates with each of the two chambers 11 of the first dual-barrel cartridge 10.

The housing 20 comprises a front retaining base 21 and a fixed portion 22. The front retaining base 21 is positioned at one end of the housing 20 and the front retaining base 21 comprises two recesses 211 positioned opposite each other. The fixed portion 22 comprises two lateral sides 221 and a first fastening component 222. Each of the two lateral sides 221 of the fixed portion 22 is respectively mounted in one of the two recesses 211 of the front retaining base 21, allowing the fixed portion 22 to be connected to the housing 20. The first fastening component 222 is positioned between the two lateral sides 221 of the fixed portion 22, and the first fastening component 222 in accordance with the present invention is a first hook.

The adaptor 30 comprises a first plate 31, two inlets 32 and two outlets 33. The first plate 31 comprises a front surface 311 and a rear surface opposite to the front surface 311. Each of the two inlets 32 is circular and separately connected to the front surface 311 of the first plate 31, and the outside diameter of each of the two inlets 32 is equal to the inside diameter of each of the two openings 12 of the first dual-barrel cartridge 10. Each of the two inlets 32 is respectively mounted into and communicates with each of the two openings 12 of the first dual-barrel cartridge 10. Each of the two outlets 33 is separately connected to the rear surface of the first plate 31, one of the two outlets 33 communicates with one of the two inlets 32, and the other of the two outlets 33 is circular and communicates with the other of the two inlets 32. Each of the two outlets 33 comprises a front outlet 331 and a back outlet 332. One end of each of the two back outlets 332 is connected to the rear surface of the first plate 31, and the other end of each of the two back outlets 332 is connected to and communicates with the front outlet 331; the outside diameter of each of the front outlets 331 is smaller than the outside diameter of each of the back outlets 332.

The second dual-barrel cartridge 40 comprises two chambers 41, two openings 42 and a second fastening component 43. Each of the two openings 42 is circular and respectively communicates with each of the two chambers 41 of the second dual-barrel cartridge 40. Each of the two openings 42 is respectively connected to and communicates with each of the two outlets 33 of the adaptor 30. The outside diameter of each of the two openings 42 of the second dual-barrel cartridge 40 is equal to the outside diameter of each of the back outlets 332. Besides, the inside diameter of each of the two openings 42 of the second dual-barrel cartridge 40 is equal to the outside diameter of each of the front outlets 331.

Each of the two front outlets 331 is respectively mounted into and communicates with each of the two openings 42 of the second dual-barrel cartridge 40, allowing each of the two openings 42 respectively to be connected to each of the back outlets 332 of the outlets 33.

The second fastening component 43 is formed between the two openings 42 of the dual-barrel cartridge 40, and the second fastening component 43 in accordance with the present invention is a second hook. The second hook of the second dual-barrel cartridge 40 is complementary to the first hook of the housing 20, allowing the adaptor 30 to be fastened between the first dual-barrel cartridge 10 and the second dual-barrel cartridge 40, and allowing the second dual-barrel cartridge 40 to be fastened with the housing 20.

With references to FIGS. 1 to 4, as a user wishes to transfer two different component substances respectively remaining in each barrel of the first dual-barrel cartridge 10 to its component channel of the second dual-barrel cartridge 40, each of the two inlets 32 of the adaptor 30 should be respectively mounted into each of the two openings 12 of the first dual-barrel cartridge 10, and each of the two front outlets 331 of the adaptor 30 should be respectively mounted into each of the two openings 42 of the second dual-barrel cartridge 40, allowing each of the two openings 12 of the first dual-barrel cartridge 10 to respectively communicate with each of the two openings 42 of the second dual-barrel cartridge 40. Then, the first hook of the housing 20 is to be fastened with the second hook of the second dual-barrel cartridge 40, allowing the second dual-barrel cartridge 40 to be connected to the adaptor 30 and the first dual-barrel cartridge 10 stably. Finally, the user can transfer the two different component substances from the first dual-barrel cartridge 10 to the second dual-barrel cartridge 40 by a portable mixer-dispenser apparatus.

In another embodiment, the outside diameter of each of the two front outlets 331 is larger than the outside diameter of each of the two back outlets 332 and the inner diameter of each of the two front outlets 331 is equal to the outside diameter of each of the two openings 42, allowing each of the two openings 42 of the second dual-barrel cartridge 40 to be respectively mounted into the two front outlets 331 of the adaptor 30.

Figure 5:
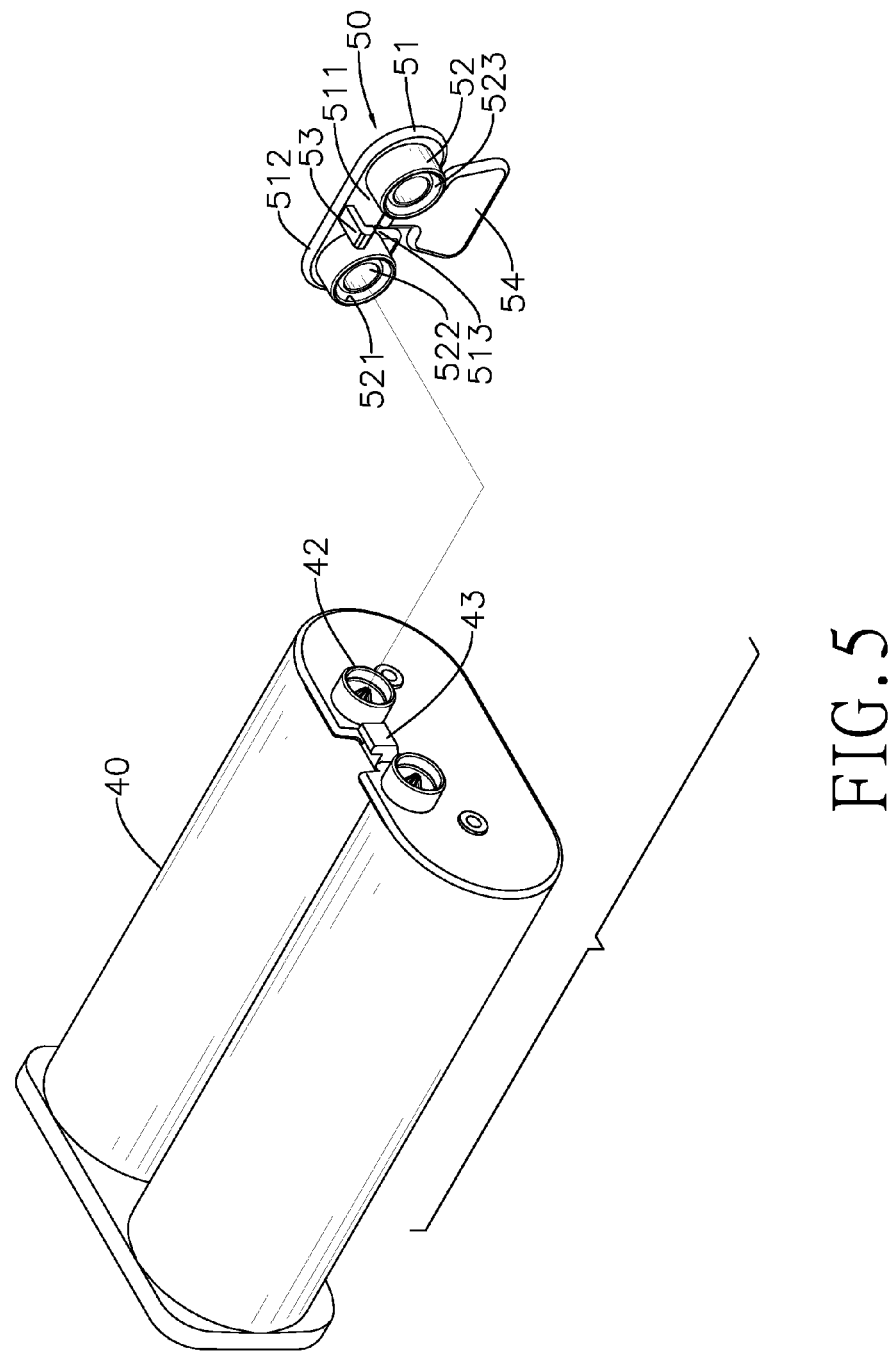
FIG. 5 is a perspective exploded view of another embodiment of the cartridge adaptor in accordance with the present invention.

In another embodiment, with references to FIG. 5, the cartridge adaptor in accordance with the present invention further comprises a lid 50. The lid 50 comprises a second plate 51, two covers 52, a third fastening component 53, and a protrusion 54. The second plate 51 comprises a surface 511, two lateral sides 512 and a groove 513. The two lateral sides 512 are disposed at side edges of the surface 511. The groove 513 is formed on one of the two lateral sides 512.

Each of the two covers 52 is circular and formed on the surface 511 and is respectively positioned besides the groove 513. Each of the two covers 52 comprises an inner wall 521, an inner protrusion 522 and a recess 523. The diameter of each of the inner walls 521 is equal to the outside diameter of each of the two openings 42 of the second dual-barrel cartridge 40. Each of the inner protrusions 522 is cylindrical and disposed within each of the two covers 52. Each of the recesses 523 is annular and positioned between the inner wall 521 and the inner protrusion 522; the diameter of each of the inner protrusions 522 is equal to the inside diameter of each of the two openings 42 of the second dual-barrel cartridge 40. Each of the two covers 52 respectively covers each of the two openings 42 of the second dual-barrel cartridge 40, allowing each of the inner protrusions 522 respectively to be mounted into each of the two openings 42, and each of the two openings 42 respectively to be disposed into each of the recesses 523 of the covers 52.

The third fastening component 53 is disposed on the surface 511 of the second plate 51. The third fastening component 53 in accordance with the present invention is a third hook. The third hook is complementary to the second hook of the second dual-barrel cartridge 40, allowing the lid 50 to be fastened with the second dual-barrel cartridge 40.

The protrusion 54 is disposed on the groove 513 of the second plate 51. It is convenient for a user to detach the third fastening component 53 of the lid 50 from the second fastening component 43 of the second dual-barrel cartridge 40 by pulling the protrusion 54 away from the second dual-barrel cartridge 40.

As the user finishes transferring the two different component substances from the first dual-barrel cartridge 10 to the second dual-barrel cartridge 40 by a portable mixer-dispenser apparatus, each of the two openings 42 of the second dual-barrel cartridge 40 is respectively covered by each of the covers 52 of the lid 50, followed by fastening the third fastening component 53 with the second fastening component 43.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A cartridge adaptor comprising:
   a first dual-barrel cartridge comprising
      two openings; and
   a housing disposed by the first dual-barrel cartridge and having
      a front retaining base positioned at one end of the housing and comprising two recesses positioned opposite each other; and
      a fixed portion comprising
         two lateral sides, wherein each of the two lateral sides of the fixed portion is mounted in a respective one of the two recesses of the front retaining base; and
         a first fastening component positioned between the two lateral sides of the fixed portion; and
   an adaptor having
      a first plate comprising
         a front surface; and
         a rear surface opposite to the front surface;
      two inlets, wherein each of the two inlets is separately connected to the front surface of the first plate, and each of the two inlets is respectively mounted into and communicates with each of the two openings of the first dual-barrel cartridge;
      two outlets, wherein each of the two outlets is separately connected to the rear surface of the first plate and one of the two outlets communicates with one of the two inlets, and the other of the two outlets communicates with the other of the two inlets; and
   a second dual-barrel cartridge comprising
      two openings, wherein each of the two openings is respectively connected to and communicates with each of the two outlets of the adaptor; and
      a second fastening component formed between the two openings of the second dual-barrel cartridge and being complementary to the first fastening component of the housing.

2. The cartridge adaptor as claimed in claim 1, wherein the cartridge adaptor further comprises
   a lid comprising
      a second plate comprising
         a surface; and
         two lateral sides disposed at side edges of the surface of the lid; and
      two covers, wherein each of the two covers is formed on the surface of the second plate; and
      a third fastening component disposed on the surface of the second plate and being complementary to the second fastening component of the second dual-barrel cartridge.

3. The cartridge adaptor as claimed in claim 2, wherein the lid further comprises a groove formed on one of the two lateral sides of the second plate.

4. The cartridge adaptor as claimed in claim 3, wherein the lid further comprises a protrusion, wherein the protrusion is disposed on the groove of the second plate.

5. The cartridge adaptor as claimed in claim 1, wherein each of the two outlets of the adaptor further comprises
   a back outlet, wherein one end of the back outlet is connected to the rear surface of the first plate; wherein the outside diameter of the back outlet is equal to the outside diameter of each of the two openings of the second dual-barrel cartridge; and
   a front outlet, wherein one end of each of the front outlets of the two outlets is respectively connected to and communicates with each of the back outlets of the two outlets opposite to the rear surface of the first plate; wherein the outside diameter of each of the front outlets is smaller than the outside diameter of each of the back outlets but is equal to the inside diameter of each of the two openings of the second dual-barrel cartridge.

6. The cartridge adaptor as claimed in claim 1, wherein each of the two outlets of the adaptor further comprises
   a back outlet, wherein one end of the back outlet is connected to the rear surface of the first plate; the outside diameter of the back outlet is equal to the outside diameter of each of the two openings of the second dual-barrel cartridge; and
   a front outlet, wherein one end of each of the front outlets is respectively connected to and communicates with each of the hack outlets; wherein the outside diameter of the front outlet is bigger than the outside diameter of the back outlet and the inner diameter of the front outlet is equal to the outside diameter of each of the two openings of the second dual-barrel cartridge.

7. The cartridge adaptor as claimed in claim 1, wherein the first fastening component of the housing is a first hook.

8. The cartridge adaptor as claimed in claim 1, wherein the second fastening component of the second dual-barrel cartridge is a second hook.

9. The cartridge adaptor as claimed in claim 2, wherein the third fastening component of the lid is a third hook.

10. The cartridge adaptor as claimed in claim 2, wherein each of the two covers further comprises
    an inner wall;
    an inner protrusion, wherein each of the inner protrusions is disposed within each of the two covers and mounted into each of the two openings of the second dual-barrel cartridge; and a recess, wherein each of the recesses is positioned between the inner wall and the inner protrusion of each of the two covers, and each of the two openings of the second dual-barrel cartridge is respectively disposed in each of the recesses.

11. The cartridge adaptor as claimed in claim 10, wherein the diameter of each of the inner protrusions of the two covers is equal to the inside diameter of each of the two openings of the second dual-barrel cartridge.

12. The cartridge adaptor as claimed in claim 10, wherein the diameter of the inner wall of each of the two covers is equal to the outside diameter of each of the two openings of the second dual-barrel cartridge.

\* \* \* \* \*